United States Patent [19]

Pedlick et al.

[11] Patent Number: 5,018,657
[45] Date of Patent: May 28, 1991

[54] PNEUMATICALLY ACTUATED SURGICAL STAPLER HEAD

[75] Inventors: Jack Pedlick, Butler; Bela Vincze; Jess Deniega, both of Flemington, all of N.J.

[73] Assignee: Ethicon, Inc., Somerville, N.J.

[21] Appl. No.: 294,523

[22] Filed: Jan. 9, 1989

[30] Foreign Application Priority Data

Jan. 15, 1988 [GB] United Kingdom ................ 8800909

[51] Int. Cl.⁵ ........................................... A41H 17/00
[52] U.S. Cl. .................................... 227/178; 227/19; 227/130
[58] Field of Search ..................... 227/8, 19, 130, 179, 227/175, 176, 177, 178

[56] References Cited

U.S. PATENT DOCUMENTS

| 3,551,987 | 1/1971 | Wilkinson | 227/178 |
| 3,613,507 | 10/1971 | Smith | 91/398 |
| 3,618,842 | 11/1971 | Bryan | 227/138 |
| 3,638,652 | 2/1972 | Kelley | 227/76 X |
| 3,643,851 | 2/1972 | Green et al. | 227/19 |
| 3,662,939 | 5/1972 | Bryan | 227/19 |
| 3,717,294 | 2/1973 | Green | 227/19 |
| 3,815,476 | 6/1974 | Green et al. | 91/410 |
| 3,836,116 | 9/1974 | Noiles | 91/398 |
| 3,837,555 | 9/1974 | Green | 227/130 |
| 4,331,277 | 5/1982 | Green | 227/19 |
| 4,349,028 | 9/1982 | Green | 227/19 |
| 4,407,432 | 10/1983 | Shichman | 222/54 |
| 4,605,004 | 8/1986 | DiGiovanovi et al. | 227/DIG. 7 |

Primary Examiner—Paul A. Bell
Attorney, Agent, or Firm—Paul A. Coletti

[57] ABSTRACT

A driving mechanism is provided as a means to clamp and implant surgical staples pneumatically. First, one pneumatic line propels a clamping piston to clamp the tissue and to propel a driving piston into position to be fired. Then a second pneumatic line causes the driving piston to propel a driver which implants staples into the tissue.

22 Claims, 3 Drawing Sheets

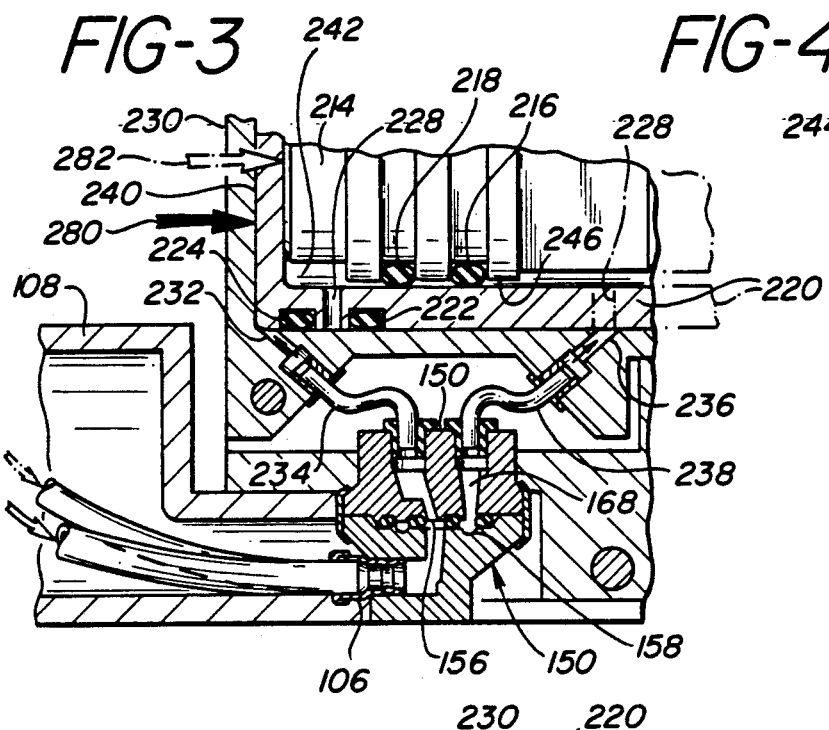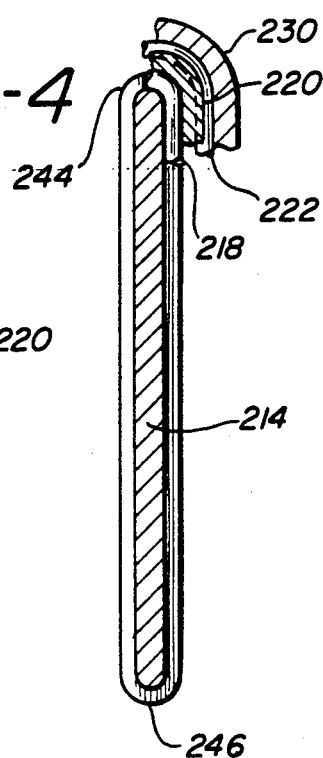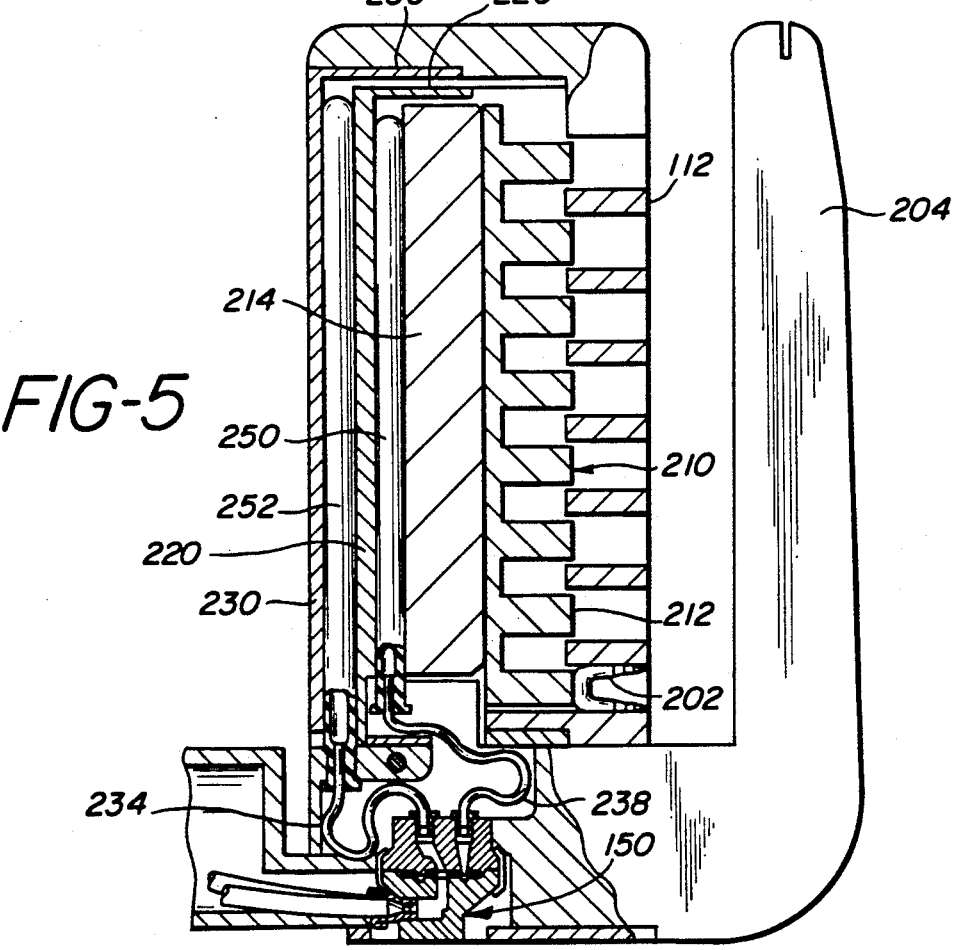

PNEUMATICALLY ACTUATED SURGICAL STAPLER HEAD

This invention relates to surgical staplers for implanting mechanical surgical fasteners in the tissue of a patient, and, in particular, to surgical staplers which are powered by pressurized gas.

Surgical staplers which implant surgical fasteners using the force of pressurized gas are known in the art, and are described in U.S. Pat. Nos. 3,837,555; 3,836,116; 3,815,476; 3,717,294; 3,662,939; 3,643,851; 3,618,842; 3,613,507; 4,407,432; 4,439,028; and 4,331,277, among others In the instruments shown in these patents, a cylinder of pressurized gas is contained in the handle of the instrument. Gas from the cylinder is conducted to a power unit at the rear of the handle, where the pressurized gas is applied to the proximal end of a mechanical linkage arrangement. The mechanical linkage is connected to a staple cartridge at the distal end of the instrument. When the trigger on the handle is depressed, pressurized gas actuates the mechanical linkage to implant a staple from the distally located cartridge.

All of the instruments shown in the above patents deliver a single staple upon each actuation of the instrument. It would be desirable for a pneumatic stapler to implant several staples at each actuation of the instrument, such as is performed by the linear stapler shown in U.S. Pat. No. 4,527,724. An instrument constructed in accordance with the present invention is capable of implanting one or more rows of staples upon each actuation of the instrument.

In the pressurized gas staplers described in the above patents, the pressure of the gas contained in the cylinder is chosen to provide the force required to operate the mechanical linkage arrangement. The linkage arrangement extends through the shaft of these instruments, between the handle of the instrument and the stapler head. Generally, the gas pressure is on the order of 100 p.s.i. a valving system conducts the pressurized gas from the cylinder to the linkage upon demand, whereby the linkage arrangement in the connecting shaft is actuated by the 100 p.s.i. gas pressure. The actuated linkage arrangement in turn activates the stapling mechanism in the stapler head to staple tissue which is clamped between the jaws of the stapler head.

It would be desirable to simplify the mechanical apparatus of these prior art devices in order to provide simpler and more versatile instruments. In particular, it would be desirable to conduct the pressurized gas directly to the stapler head, thereby obviating the need for the mechanical linkage arrangement between the source of pressurized gas in the handle of the instrument and the stapler head. A further advantage resulting from such an approach is that the shaft of the instrument which connects handle to the stapler head can be made flexible, since its purpose in such an improved instrument would be to connect flexible pneumatic tubing to the stapler head, instead of conducting a rigid linkage arrangement as in the prior art devices.

In accordance with the principles of the present invention, pneumatic surgical staplers are provided having surgical stapler heads which are responsive to pressurized gas to clamp tissue between the jaws of the stapler head and implant staples in the clamped tissue. In a first embodiment, a surgical stapler head suitable for implanting a row of surgical staples in tissue is configured in a double piston arrangement. Upon a first actuation of the instrument, pressurized gas drives a first one of the pistons against the tissue to clamp the tissue between the jaws of the stapler head. A second actuation of the instrument causes the second piston to drive a staple driver, which implants the staples in the tissue. In a preferred first embodiment, the ends of the piston are rounded to prevent piston binding and insure pneumatic integrity.

In accordance with the principles of a preferred embodiment of the present invention, the clamping and drive pistons of the first embodiment are actuated by balloon-like bladders located behind each piston. Upon a first actuation of the instrument, a first bladder is inflated and its expansion drives the clamping piston to clamP tissue between the jaws of the stapler head. A second actuation of the instrument inflates the second bladder to driver the staple driver piston, which implants the staples in the tissue. This second embodiment obviates the need to provide pneumatic sealing around the two pistons, thereby easing design tolerances and further simplifying the construction and operation of the instrument.

The embodiments of the present invention are advantageous over prior art pneumatic staplers which deliver pressurized gas to mechanical stapling mechanisms in the handle and shaft portions of the instrument. In such prior art staplers, considerable energy is expended in actuating mechanical linkages extending from the handle and through the shaft to the stapler head. In the present invention, the gas pressure is delivered directly at the stapler head. Thus, there is no ambiguity as to the force delivered during clamping and stapling since the pressure regulated gas is delivered directly at the clamping and stapling members without energy loss. In the drawings:

FIG. 3 is an enlarged view of a portion of FIG. 2;

FIG. 4 is a frontal view of the stapler head of FIG. 2 showing the rounded piston ends;

FIG. 5 is a partial cross-sectional view of a second embodiment of a stapler head of the present invention.

Figure 1:
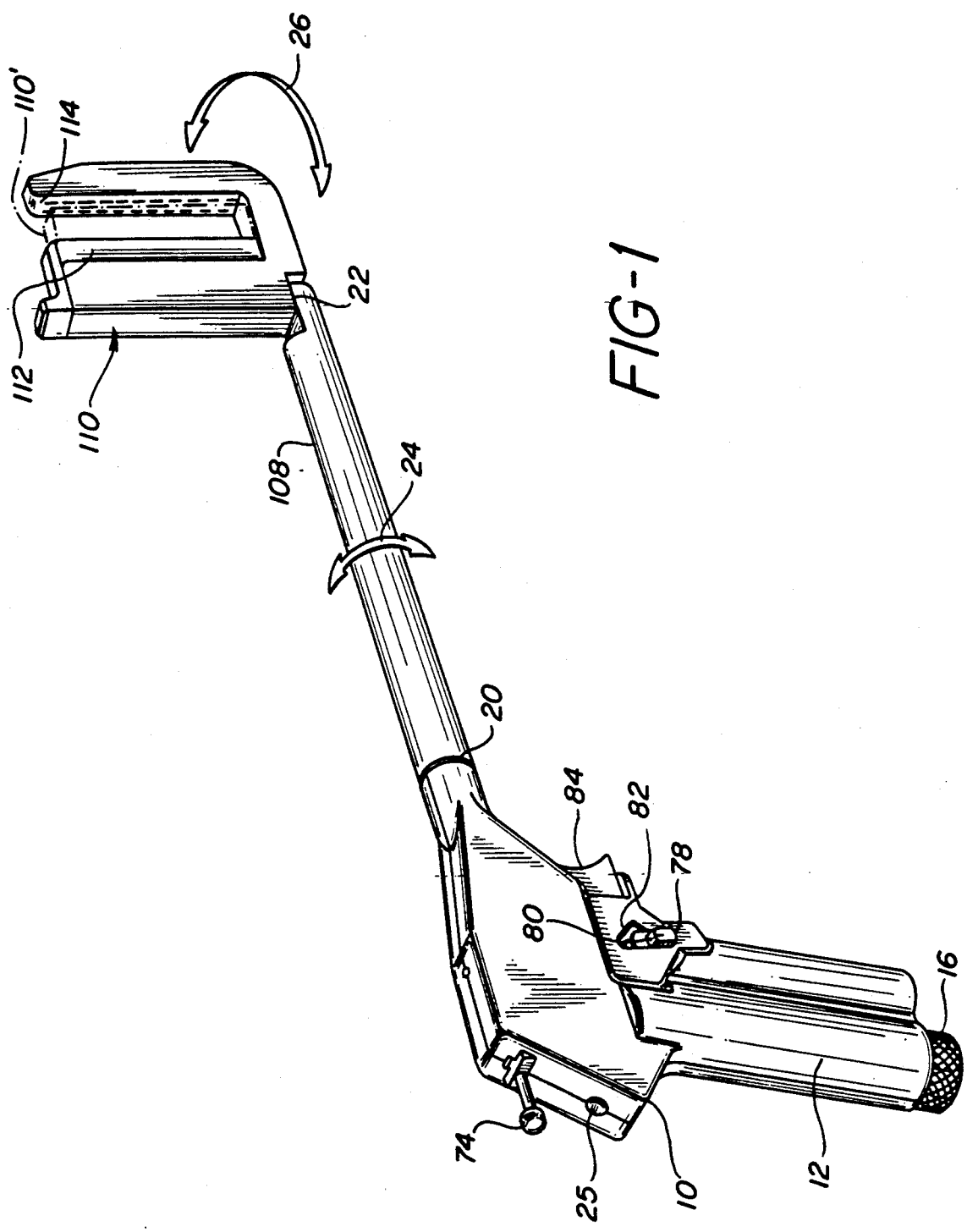
FIG. 1 is a perspective view of a surgical stapler constructed in accordance with the principles of the present invention.

Referring first to FIG. 1, a pneumatically actuated surgical stapler of the present invention is shown. The stapler includes three major components: a handle portion 10, a shaft Portion 108, and a stapler head 110. The three components are joined at their interconnecting points by pneumatic quick-disconnect fittings which allow the components to be disconnected and interchanged with shafts and stapler heads of other configurations. Also located at the joints 20 and 22 are pneumatic rotatable unions which allow free rotation of the major components of the stapler with respect to each other, as indicated by the arrows 24 and 26. Specifically, the shaft 108 is free to rotate completely about its axis at the joint 20 as indicated by arrow 24. The stapler head 110 is free to rotate greater than 200° about an axis which is normal to the axis of the shaft 108, as indicated by arrow 26.

A cylinder of pressurized gas is inserted into the lower portion 12 of the handle 10 by removing the cap 16 and inserting the cylinder into the handle. Once the cylinder has been inserted and the cap 16 tightened, gas from the cylinder is released and flows to a pressure regulator in the handle. The release of gas from the cylinder arms the stapler and causes a button 25 to extend a short distance out the rear of the handle, indicating to the use that the stapler is pressurized.

The first step in a stapling procedure is to clamp the tissue to be stapled between the jaws of the stapler head 110. The tissue is located between the jaws, and a slide 74 which extends from the rear of the stapler is depressed. When the slide is pressed forward, pressurized gas is allowed to flow to the stapler head through a first gas line to clamp the tissue between the jaws of the stapler head. As soon as the slide 74 is released, it slides back to its illustrated extended position by spring force. The position of the rearward portion of the stapler head after clamping is shown in phantom at 110' in FIG. 1.

Staples in a cartridge 112 may then be driven through the clamped tissue by depressing the trigger 84 of the handle. Before the trigger can be depressed, however, a trigger safety 78 must be moved upward in its slot 80 from the position shown in FIG. 1 and rotated into a forward extension 82 of the slot 80. This safety mechanism prevents inadvertent placement of the staples before the user is ready to do so. After the trigger safety 78 has been moved up and rotated forward the trigger may be depressed to implant the staples in the tissue, either by clinching the legs of the staples against an anvil 114 in the stapler head 110 or by interlocking the legs of the staples with connecting staple receivers located in the position of the anvil. As the trigger 84 is depressed, the trigger safety is rotated back to its more vertical position and slides downward in slot 80 by spring force.

Figure 2:
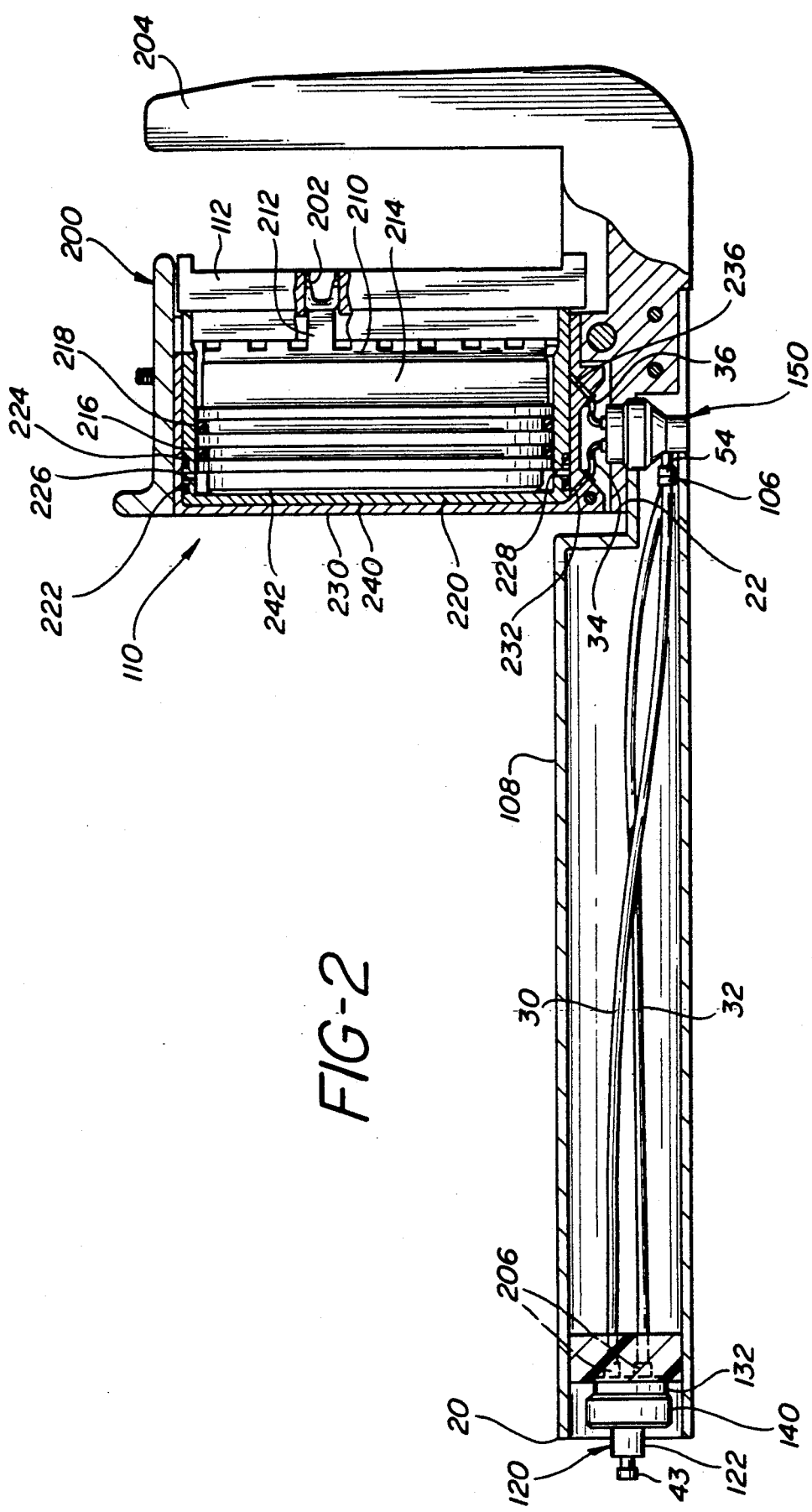
FIG. 2 shows the shaft and stapler head of a surgical stapler employing a stapler head constructed in accordance with the principles of the present invention.

FIG. 2 is a partial cross-sectional illustration of shaft 108 and stapler head 110 of the present invention. The stapler head includes a jaw 200 which carries a plurality of staples 202 in a movable clamping and stapling mechanism. Opposite the jaw 200 is a stationary opposing jaw 204. The face of the stationary jaw which opposes the stapling mechanism comprises an anvil which clinches or bends the legs of metal staples which pass through the tissue between the jaws. Alternatively, when the staples are formed of absorbable polymeric materials, the stationary jaw carries a cartridge of receivers which mate with and retain the legs of the polymeric staples. Such polymeric staples and receivers are described in U.S. patent application Ser. No. 117,592, filed Nov. 5, 1987.

The staples 202 are located in pockets formed in a staple cartridge 112 on the jaw 200, with the legs of the staples directed toward the stationary jaw 204. Behind the staple cartridge 112 is a staple pusher 210. The staple pusher has fingers 212 which are directed toward the crowns of respective staples in the staple cartridge. Behind the staple pusher 210 is a driver piston 214. The driver piston is located inside a clamping piston 220, and is pneumatically sealed therein by two circumferential O-rings 216 and 218, shown in enlarged detail in FIG. 3. The clamping piston 220 is located inside a piston housing 230. The clamping piston 220 is pneumatically sealed inside the piston housing by two circumferential O-rings 222 and 224, also shown in FIG. 3. Between the latter two O-rings are ports 226 and 228 which pass through the clamping piston. These ports are symmetrically located so that the clamping piston can be inserted into the piston housing with either end at the bottom.

Located at the rear of the piston housing is a passageway 232. This passageway is connected to a first connector of right angle pneumatic union 150 by a pneumatic tubing segment 34. Toward the front of the piston housing is a second passageway 236. This passageway is connected to a second connector of union 150 by tubing segment 36.

To the lower left of the stapler head 110 is the shaft portion 108 of the stapler. The shaft 108 includes two sections 30 and 32 of pneumatic tubing. The tubing in the shaft portion is connected to two inlet ports of the right angle union 150 (one of which is shown at 54) by pneumatic snap fittings, one of which is shown at 106. At the rear terminus of the shaft 108, which is to be connected to the handle 10, is a parallel pneumatic union 120. Pneumatic union 120 is removably connected to the handle by pneumatic snap fittings, one of which is shown at 43. The pneumatic tubing 30, 32 is connected to two outlet ports 112 of the connector 120.

When tissue to be stapled is located between the jaws 200 and 204 of the stapler head and it is desired to clamp the tissue between the jaws, the slide 74 is depressed and pressurized gas flows from the handle and into one port of the parallel union 120. The pressurized gas is carried through tubing section 30 in the shaft portion 108 and through a passageway of the right angle union 150. The pressurized gas passes through tubing segment 34 and passageway 232 to the rear of the clamping piston 220. There the gas is forced into the interface 240 between the clamping piston and the piston housing, where it expands and pushes the clamping piston forward as indicated by the arrow 280 toward the stationary jaw. As the clamping piston moves, it carries the driver piston, staple pusher, and staple cartridge with it. This will clamp the tissue between the staple cartridge and the stationary jaw 204. The clamping piston 220 is now in a position in the housing 230 such that the front passageway 236 opposes port 228 of the clamping piston as indicated in phantom in FIG. 3. It should be noted that, to avoid the need to precisely align this passageway and port, and thereby permit the clamping and stapling of tissues of various thicknesses, the port 228 may be longitudinally widened into the form of a slot. Alignment of passageway 236 with any portion of the slot will thereby enable the pneumatic coupling of the passageway 236 to the space at the rear of the driver piston.

With the tissue securely clamped between the jaws, the user moves and rotates the trigger safety and pulls the trigger to implant the staples. Pressurized gas flows through parallel union 120, pneumatic tubing 32, the connector 150, and tubing segment 36 to passageway 236. The pressurized gas then flows through port 228 in the clamping piston and into space 242 at the rear of the driver piston. The expanding gas in this space pushes the driver piston 214 forward against the rear of the staple pusher 210 as indicated by arrow 282, whereby uniform pressure is applied to the pusher and its fingers. The fingers then drive the staples out of the pockets of the staple cartridge, through the tissue, and against the anvil or into the receivers of the stationary jaw. When the trigger is released, the pressurized gas to the driver piston and clamping piston is vented through the handle, releasing the jaw 200 from the stapled tissue.

It has been found that when rectangular shaped pistons are used for the clamping and driver pistons, the pistons will tend to bind as they move relative to the piston housing and each other. Also, the O-ring seals at the corners of the rectangular pistons do not provide adequate pneumatic sealing. Accordingly, the ends of the pistons and the piston housing are rounded in an oval shape as shown at 244 and 246 in FIG. 4. This eliminates the binding problem and provides good O-ring seals at the piston ends.

The embodiment of the present invention of FIG. 5 is similar to that of FIGS. 2 and 3, and shows an alternate stapler head embodiment using balloon-like bladders. A driver bladder 250 is connected to tubing segment 238 and is located behind the driver piston 214 inside the clamping piston 220. The tubing segment 238 is connected to an outlet port of the right angle union 150. A clamping bladder 252 is connected to tubing segment 234 and is located behind the clamping piston 220 inside the piston housing 230. The tubing segment 234 is connect to a second outlet port of the right angle union 150. As the clamping bladder 252 is inflated when the slide 72 is depressed, it expands and pushes the clamping piston 220 toward the stationary jaw 204 to clamp tissue between the jaws. When the trigger is depressed the driver bladder 250 is inflated, driving the driver piston 214 against the staple pusher and implanting the staples in the tissue. The use of the bladders obviates the need for O-ring seals around the pistons, which in this embodiment have no pneumatic properties. This embodiment allows the use of fully rectangular pistons, as the tolerances between the non-pneumatic pistons can be relaxed so as to prevent piston binding. The use of the bladder actuators also provides this embodiment with an inherent safety feature. In the event of an inadvertent overpressurization of the bladders, the bladders will burst inside the housing and pistons. The force of this occurrence will be confined within the housing of the stapler head, and the escaping gas will be vented harmlessly out through the interfaces between the pistons and the housing due to the relaxed tolerances therebetween. Moreover, this second embodiment is capable of stapling tissue of a wide variety of thicknesses, as the tubing segment 238 is free to move in concert with the two pistons over a wide range of clamping positions as the pistons move during the clamping procedure.

What is claimed is:

1. A surgical stapling instrument comprising:
   a source of pressurized gas;
   pneumatic means for clamping tissue;
   pneumatic means for implanting staples in said clamped tissue; and
   manual means for actuating said pneumatic clamping means and said pneumatic staple implanting means by pressurized gas from said source.

2. The surgical stapling instrument of claim 1, wherein said manual actuating means includes a trigger which is actuated to deliver pressurized gas to said staple implanting means, and a manual control which is actuated to deliver pressurized gas to said clamping means.

3. The surgical stapling instrument of claim 1, wherein each of said clamping means and said staple implanting means includes a pneumatic piston.

4. The surgical stapling instrument of claim 1, wherein each of said clamping means and said staple implanting means are actuated by the inflation of a bladder.

5. In a surgical stapler having an actuation mechanism connected to a driving mechanism by means of a pneumatic stapling line, said driving mechanism including a stapler driver and a stapling surface, the improvement comprising:
   a pneumatic clamping line attached to said actuation mechanism and containing a clamping piston attached to said pneumatic clamping line, said clamping piston capable of propelling said driver toward said stapling surface to tissue between said driver and said stapling surface, and
   a driving piston to propel said driver, said driving piston attached to said pneumatic stapling line.

6. The surgical stapler of claim 5 wherein said driving piston is seated within said clamping piston and separated therefrom by means of an O-ring seal to form a pneumatic chamber behind said driving piston.

7. The surgical stapler of claim 6 wherein said clamping piston is seated within an O-ring seal within a piston housing such that there is formed a clamping chamber behind said clamping piston within said housing.

8. The surgical stapler of claim 7 wherein said driving piston and said clamping piston exhibit generally oval corners.

9. The surgical stapler of claim 5 wherein said pneumatic clamping line propels said clamping piston by means of a clamping bladder seated behind said clamping piston within a piston housing, said bladder being filled by said pneumatic clamping line to drive said clamping piston when activated by said actuation mechanism.

10. The surgical stapler of claim 9 wherein said driving piston is movably contained within said clamping piston, said driving piston propelled by the inflation of a driving bladder seated behind said driving piston upon actuation of said actuation mechanism.

11. The surgical stapler of claim 10 wherein said driving piston and said clamping piston exhibit generally oval corners.

12. The surgical stapler of claim 10 wherein said driving piston and said clamping piston are generally rectangular.

13. The surgical stapler of claim 5 further comprising:
   a housing enveloping said clamping piston, said driving piston and said driver in one contiguous unit, said clamping piston further enveloping said driving piston;
   wherein said pneumatic clamping line is capable of filling a clamping chamber within said housing to propel said clamping piston, and said pneumatic stapling line is capable of filling a stapling chamber separate from said clamping chamber within said housing to propel said driving piston.

14. The surgical stapler of claim 13 wherein said Pneumatic clamping line propels said clamping piston by means of a clamping bladder seated behind said clamping piston within said housing, said bladder being filled by said clamping line to drive said clamping piston on activation by said actuating mechanism.

15. In a surgical stapler having an actuating mechanism connected to a driving mechanism by means of a pneumatic clamping line and a pneumatic stapling line, said driving mechanism including a driver capable of driving staples toward a stapling surface, the improvement comprising:
   a driving piston to propel said driver, said driving piston actuated by said pneumatic stapling line;
   a clamping piston actuated by said pneumatic clamping line, said clamping piston capable of propelling said driving piston and said driver toward said stapling surface to clamp tissue between said driver and said stapling surface; and
   a piston housing enveloping said clamping piston, said driving piston, and said driver in one contiguous unit, said clamping piston enveloping said driving piston within said piston housing, said housing defining a clamping chamber connected to said pneumatic clamping line and a driving chamber separated from said clamping chamber and forward of said clamping chamber toward said stapling surface, said driving chamber connected to said pneumatic driving line;

wherein said pneumatic clamping line is activated by said actuating mechanism to fill said clamping chamber pneumatically to propel said clamping piston toward said stapling surface to clamp tissue between said driver and said stapling surface, and said pneumatic driving line can thereafter be activated to fill said driving chamber pneumatically to propel said driving piston, said driver, and said staples toward said stapling surface to implant said staples in said tissue.

16. The surgical stapler of claim 15 wherein said driving piston is separated from said clamping piston by means of an O-ring seal seated between said clamping piston and said driving piston.

17. The surgical stapler of claim 16 wherein said clamping piston is separated from said piston housing by means of an O-ring seal seated between said housing and said clamping piston.

18. The surgical stapler of claim 17 wherein said driving piston and said clamping piston exhibit generally oval ends.

19. The surgical stapler of claim 18 wherein said pneumatic clamping line is connected to said clamping chamber by means of a clamping passageway extending through said housing, and said pneumatic driving line is connected to said driving chamber by means of a driving passageway extending into said driving chamber.

20. The surgical stapler of claim 16 wherein said pneumatic clamping line propels said clamping piston by means of a clamping bladder located behind said clamping piston within said housing, said bladder being inflated by said clamping line upon activation of said actuating mechanism to drive said clamping piston.

21. The surgical stapler of claim 20 wherein said driving piston is enveloped by said clamping piston, said driving piston propelled by said pneumatic driving line by means of a driving bladder seated behind said driving piston, said driving bladder being inflated upon activation of said actuating mechanism to drive said driving piston.

22. The surgical stapler of claim 21 wherein said Pneumatic clamping line is connected to said clamping bladder by means of a clamping passageway within said housing and said pneumatic driving line is connected to said driving bladder by means of a driving passageway within said housing forward of said clamping passageway toward said stapling surface.

* * * * *